United States Patent [19]

Ohms et al.

[11] Patent Number: 5,019,348

[45] Date of Patent: May 28, 1991

[54] AUTOMATED CHEMICAL CONVERSION UNIT IN A PEPTIDE/PROTEIN SEQUENATOR

[75] Inventors: Jack I. Ohms; Majid Qadeer, both of Palo Alto; Harry A. Penhasi, Cupertino, all of Calif.

[73] Assignee: Beckman Instruments, Inc., Fullerton, Calif.

[21] Appl. No.: 303,004

[22] Filed: Jan. 26, 1989

Related U.S. Application Data

[63] Continuation of Ser. No. 203,577, May 26, 1988, abandoned, which is a continuation of Ser. No. 782,619, Oct. 1, 1985, abandoned, which is a continuation of Ser. No. 500,670, Jun. 3, 1983, abandoned.

[51] Int. Cl.$^5$ .............................. G01N 35/06
[52] U.S. Cl. ...................................... 422/63; 422/64; 422/116; 422/131; 436/89
[58] Field of Search ................ 422/63, 64, 116, 131; 436/89

[56] References Cited

U.S. PATENT DOCUMENTS

| | | | |
|---|---|---|---|
| 3,556,731 | 1/1971 | Martin | 422/102 X |
| 3,725,010 | 4/1973 | Penhasi | 436/89 X |
| 3,948,605 | 4/1976 | Atwood et al. | 422/63 |
| 4,011,048 | 3/1977 | Johnson, Jr. et al. | 422/63 |
| 4,115,714 | 5/1979 | Bonner et al. | 436/89 X |
| 4,351,799 | 9/1982 | Gross et al. | 422/64 X |
| 4,610,847 | 9/1986 | Hood et al. | 436/89 X |

OTHER PUBLICATIONS

Edman et al., Eur. J. Biochem, vol. 1:80 (1970).
"Method for Determination of the Amino Acid Sequence in Peptides", Pehr PehrPehr Edman, (1950), Acta Chem. Scand., vol. 4, pp. 283-293.
"Human Fibronopeptides Isolation, Characterization and Structure," B. Blomback, et al., (1966), BioChim. Biophys. Acta, vol. 115, pp. 371-396.
"The Amino Acid Sequence of Porcine Thyrocalcitonin," J. T. Potts, Jr., et al., (1968), Proc. N.A.S., vol. 59, pp. 1321-1328.
"Sequential Analysis of Proteins and Peptides," Niall Fractions, No. 2, 1969.
"P-6 Auto Converter Instruction Manual," Sequeinat, Inc., Watertown, Mass., Jan. 1, 1978.
B. Wittman-Liebold, et al., "A Device Coupled to a Modified Sequenator for the Automated Conversion of Anilinothiazolinones in PTH Amino Acids," *Analytical Biochemistry*, vol. 75, pp. 621-633 (1976).
John Bridgen, "Automated Conversion of Anilinothiazolinones into PTH Derivatives," Proceedings of the Third International Conference on Solid Phase Methods in Protein Sequence Analysis, Germany 1979.
Werner, Machleidt & Helmut Hofner, "Fully Automated Solid Phase Sequencing with On-Line Identification of PTHS by High Pressure Liquid Chromatography,"*Methods in Enzymology*, vol. XLVII (Enzyme Structure, Part E), Ed. Chw. Hirs. & Serge N. Timasheff, Academic Press (1977), pp. 33-47.

Primary Examiner—Robert J. Hill, Jr.
Attorney, Agent, or Firm—William H. May; Paul R. Harder; Wen Liu

[57] ABSTRACT

An automated chemical conversion unit for use in a peptide/protein sequencing process. The improved conversion methodology decreases the time necessary for the conversion reaction chemistry of the specific derivative of the sequenced amino acid to a more stable form. The conversion reaction is designed to be performed directly in a fraction collector tube which operates in one embodiment in conjunction with a thermoelectric temperature element to allow utilization of different temperature levels for different amino acid derivatives.

9 Claims, 5 Drawing Sheets

AUTOMATED CHEMICAL CONVERSION UNIT IN A PEPTIDE/PROTEIN SEQUENATOR

This application is a continuation of application Ser. No. 203,577, filed May, 26, 1988, now abandoned, which is a continuation of application Ser. No. 782,619, filed Oct. 1, 1985, now abandoned, which is a continuation of application Ser. No. 500,670, filed June 3, 1983, now abandoned.

BACKGROUND OF THE INVENTION

This invention relates to an improved method for performing the sequential degradation of peptide chains for the purposes of analyzing the constituents of the chains and, more particularly, is directed to the added automated capability of the conversion reaction of the Edman chemistry.

It is important to analyze the amino acid sequence of proteins and peptides in order to understand their biological functions. For example, the function of insulin is dependent upon its particular amino acid sequence. A variety of techniques may be used to determine the linear order of amino acids. One of the most important sequential methods now being used is called the Edman process. The Edman process was originally described in Acta Chem. Scand. 4, 283 (1950). Four later articles describe a general form of its use: Blomback et al., "Human Fibrinopeptides Isolation, Characterization, and Structure," Biochem, Biophys. Acta, 115 (1966) 371-396; Edman and Begg, "A Protein Sequenator," European J. Biochem. 1 (1967) 80-91; Niall et al., "The Amino Acid Sequence of Porcine Thyrocalciton", Proc. of the National Academy of Sciences, Vol. 59 No. 4, pp. 1,321-1,328, April 1968; and Niall, "Sequential Analysis of Proteins and Peptides" Fractions No. 2, pp. 1-10 (1969). Briefly, as discussed in the last article and as shown inside the cover of the Fractions publication, the Edman sequential degradation processes involve three stages: coupling, cleavage, and conversion. In the coupling stage phenyl isothiocyanate (PITC) reacts with the N-terminal amino group of the peptide to form the phenylthiocarbamyl (PTC) derivative. The pH is normally maintained at between 9 and 10 and preferably between 9 and 9.5 for the coupling reaction. In the cleavage step anhydrous acid is used to cleave the PTC derivative, i.e., the anilinothiazolinone (ATZ). After extraction of the thiazolinone the residual peptide is ready for the next cycle of coupling and cleavage reactions. Aqueous acid is used to convert the thiazolinone to the phenylthiohydantoin (PTH) which may be analyzed in an appropriate manner such as by chromatography.

At the end of the coupling step the excess PITC and the organic constituents of the coupling buffer, which is used to maintain the desired environment (such as pH) for the coupling reaction, are removed by extraction with benzene. Certain breakdown products of PITC such as aniline and phenylthiourea are also removed. Diphenylthiourea, another side product, is poorly soluble in benzene but may be removed by further extraction with a more polar organic solvent such as ethyl or butyl acetate. The water from the coupling buffer must also be removed, for example by lyophilization. The reaction vessel is then subjected to a vacuum purging operation to remove any remaining undesired materials and the dried protein as its PTC derivative is then ready for cleavage.

During the cleavage operation the protein is dissolved in anhydrous acid, for example trifluoroacetic acid. Thus, there is a strong shift in pH from basic for the coupling reaction to acidic for the cleavage reaction. The acid is then evaporated and the cleaved thiazolinone derivative is extracted from the residual peptide with butyl chloride or ethylene dichloride. After evaporation of residual solvent and a further vacuum purging operation, the peptide or protein, now one residue shorter, is ready for the next cycle.

In the typical apparatus used to perform the coupling and cleavage steps, each series constituting a cycle, the steps may be broken down into seven stages. A typical apparatus for accomplishing this is the Beckman Protein Peptide Sequencer. The first of the seven stages is the coupling of the protein. This is followed by two wash stages giving precipitation of the sample along with a primary extraction of excess reagents. The cleavage stage, cleaving the amino acid residue on the end of the protein comes next. This is followed by a first extraction which extracts the cleaved amino acid residue. If desired, to be sure that all of the amino acid residue has been cleaved, a second cleavage step may be used followed by a second extraction step.

Reference is made to U.S. Pat. No. 3,725,010 which describes in detail the above-referenced Beckman Protein Peptide Sequencer. This particular type of automatic protein/peptide sequenator avoided or minimized many of the difficulties and limitations experienced by the early efforts to automate a process for determining the amino acid sequence in protein. Several drawbacks were evident in the Edman protein sequenator. The Beckman sequencer includes a reaction cell or chamber having a rotating or spinning cup driven with the chamber. The chamber has to be properly insulated and sealed in order to ensure proper operation. In fluid communication with the reaction chamber are means for introducing and removing gases and liquids. Insulation of the chamber is necessary in order to provide a constant, uniform temperature critical for the reaction. Also, it is necessary to properly seal the reaction chamber so that during the evacuation step for waste removal and for drying, the proper vacuum environment is maintained within the chamber without having any degrading influence from the surrounding atmosphere. Consequently, it is necessary to specifically design a properly sealed driving mechanism for the spinning cup to ensure the vacuum environment within the reaction chamber. One approach as shown in the referenced patent is a magnetic coupling drive unit which is properly sealed. Included within the system are numerous vacuum seals that are necessary in order to ensure the proper environment when the vacuum is necessary. Also, rather high quality and precise vacuum pumps are necessary in order to provide the requisite vacuum when necessary. Also included are numerous vacuum lines and valves. All of this equipment to support the vacuum necessary in the reaction chamber requires a significant maintenance over a period of time.

Reference is made to copending patent application Ser. No. 458,226 filed on Jan. 14, 1983, entitled "An Improved Apparatus for Sequencing Peptides and Proteins", having the same inventors as the present application and assigned to the same assignee as the present invention. In this referenced copending patent application, discussion is directed to an improved apparatus which does not require a vacuum for operating the system. This reduces the maintenance requirements with respect to having numerous vacuum lines, valves and vacuum pumps.

When using the Edman chemistry with systems discussed and referenced in the above copending patent application, one area of the chemistry which is typically not done automatically, but is done manually, is the chemical conversion of the labile anilinothiazolinone derivative of the sequenced amino acid to a more stable phenylthiohydantoin form. This manual conversion process is done outside of the instrument by a technician.

Some existing instruments have incorporated a reaction chamber in which the conversion process occurs. Reference is made to U.S. Pat. No. 3,959,307 which utilizes an intermediate reaction vessel. A complex glass blown vessel is used as the conversion reaction vessel and is wrapped in a water bath. This glass blown reaction vessel with a water bath sheath requires considerable glass blowing artwork. This particular type of device only allows the thermostatting of the conversion process at a single temperature. In addition, the placement of an intermediate reaction vessel between the reaction chamber and the fraction collector results in fluid flow resistance added to the connectors during liquid transfers because of the low differential pressure utilized in the instrument. Further, this intermediate reaction vessel being common for each cycle would tend to contribute to cross contamination between successive cycles of the reaction process unless the vessel is thoroughly washed at the completion of each cycle.

Another system which attempts to somewhat automate the conversion process is the Sequamat P-6 Autoconverter which is discussed in the Sequemat P6 Auto Converter Instruction Manual, Jan. 1, 1978. This particular system uses an intermediate reaction vessel between the spinning cup of the reaction chamber and the fraction collector. This requires added length of the fluid transfer system and more fittings which will create a flow resistance during the transfer of the anilinothiazolinone derivative from the sequencer spinning cup. By using an intermediate reaction vessel it is necessary to provide solvent washing after each conversion so that there is no cross-contamination of the fractions.

It should also be noted with respect to the above-described existing methods for automating the conversion step a control of temperature that must be accomplished by means of circulating water or air systems. As a result, the reaction time for temperature change during the conversion process is limited. The utilization of different temperature levels is somewhat restricted because of the limited temperature change response with a circulating water or air system. These systems require additional fittings and added delivery tubing incorporated into a reaction vessel.

SUMMARY OF THE INVENTION

The present invention comprises an apparatus which allows for the Edman conversion reaction chemistry to be performed directly and automatically in a fraction collector tube or unit. The apparatus incorporates means to move a plurality of fraction collector tubes sequentially into engagement with a tube delivery head for receipt of successive amino acid fractions from the spinning cup of the reaction chamber. Once the desired conversion occurs, the fraction collector tube can be removed from the delivery head and another fraction collector tube moved into engagement with the delivery head for the next conversion process. The operation of the entire approach is included in a programmable controller to perform the desired thermal profile, time delivery of reagents and inert gas, positioning of the tubes at the delivery head and the operation of the thermoelectric device.

In one embodiment the collector tube is removably engaged by a thermoelectric case to regulate the temperature of the collector tube. The best temperature for the evaporation of liquids from the tube can be established. In addition, the required higher temperature for the actual chemical conversion can be provided.

The utilization of the fraction collector tube as the chamber for the chemical conversion eliminates the need for any separate or intermediate reaction vessel as shown in the prior art. Also, the fact that a separate fraction collection tube or unit is used for each conversion process eliminates the need for any washing because each tube contains its own resultant conversion sample. As a result, the fraction tube is not only the collector, but also the vessel for the conversion process as well as a storage vessel.

By not utilizing an intermediate reaction vessel all requirements for additional tubing and valving are eliminated. Consequently, the overall system is much more simplified. Although a heater block is all that may be necessary to provide the requisite temperature control, a thermoelectric device may also be used to regulate the temperature of the collector tube and provides rapid response to the desired temperature setting. This would eliminate the tubing, valving and additional elements in a system which would otherwise require an air or water bath. The temperature control with the thermoelectric device would be readily variable and programmable while in prior devices the thermostatted reaction vessels with water or air baths is done at a single temperature.

DETAILED DESCRIPTION OF THE INVENTION

Figure 1:
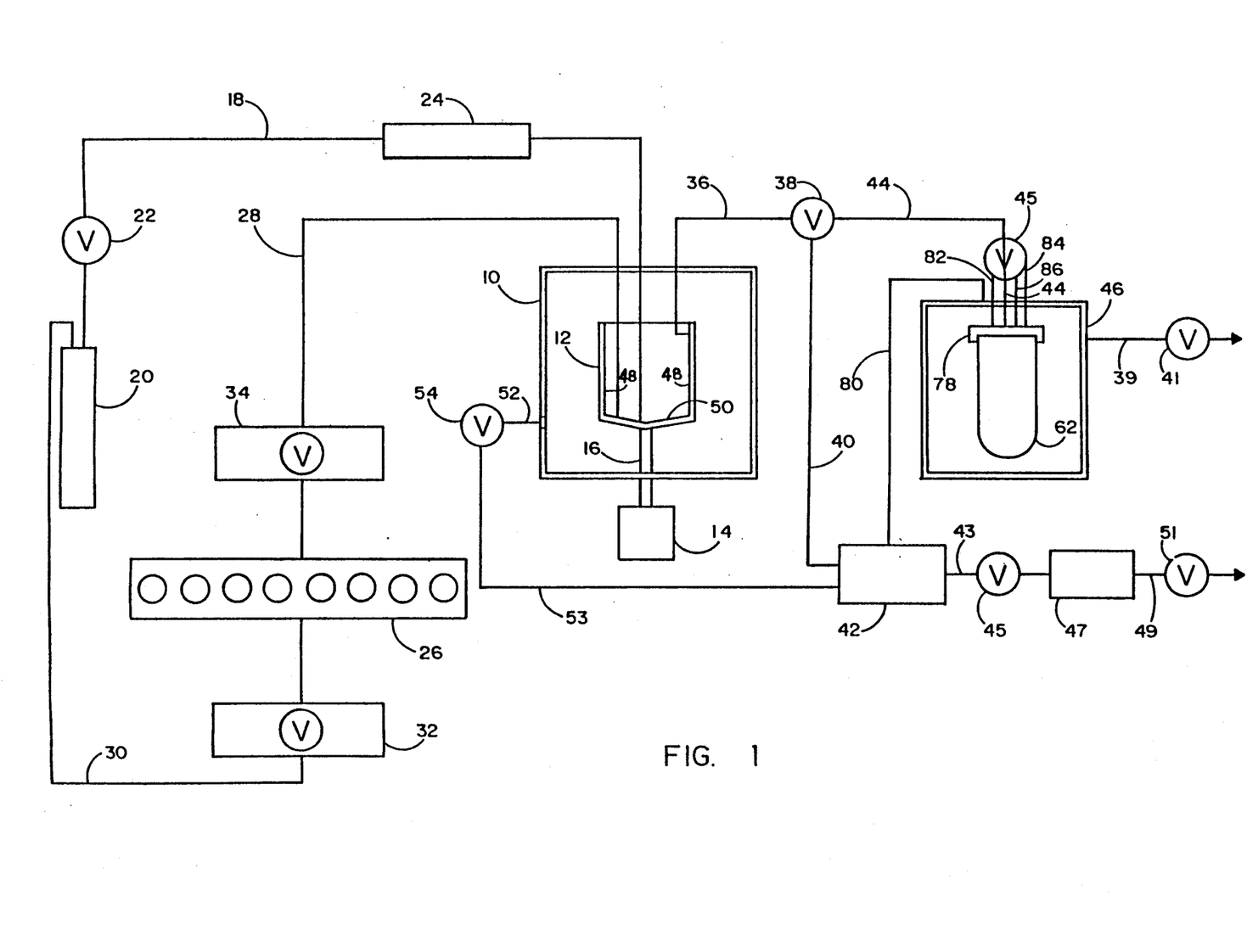
FIG. 1 is a schematic of a sequencer system.

An example of an automatic amino acid sequencer is shown schematically in FIG. 1. This particular type of sequencer system is directed to a no-vacuum system, but the application of the present invention is equally pertinent to a sequencer system having a vacuum system such as that described in the referenced U.S. Pat. No. 3,725,010.

As shown in the FIG. 1, the sequencer utilizes a reaction chamber 10 having a reaction cell or cup 12. The reaction chamber 10 is heated to a desired temperature for the reaction cycle during the sequencing operation. The reaction cell 12 is designed to rotate during the operation of the sequencing cycle and is driven by some type of motor means 14 connected by a shaft 16 to the spinning cup 12.

Reference is made to U.S. Pat. No. 3,725,010 for more detail with respect to the reaction chamber and the reaction cell. Connected in fluid communication by the transfer line 18 to the reaction cell 12 is an inert gas supply 20 such as nitrogen under positive pressure. The nitrogen passes through the line 18, a valve mechanism 22, and a preheater 24 before entering the lower portion of the spinning cell 12.

In the sequencing system there are a plurality of reagent and solvent supplies 26 which also are connected through a single or a plurality of transfer lines represented in FIG. 1 by a single line 28 to the reaction chamber 10 and into the reaction cell 12. The transfer of the reagents or the solvents is accomplished by the inert gas flow through a transfer line 30 from the inert gas supply 20 through a valve system 32. The operation of the inert gas through the valve system 32 into the reagent/solvent supply 26 and through the valve system 34 is explained in more detail in the above-referenced U.S. Pat. No. 3,725,010. The positive pressure of the inert gas provides a force to move the liquid solvent or reagent into the reaction cell 12 at the proper time during the sequencing cycle.

Removal of vapors during the reaction cycle is accomplished through the extraction line 36 which leads to a valve 38. The vapor is then directed through the waste line 40 into a waste container 42 for transfer to exhaust or another waste area. In a preferable arrangement vapor may exit the waste container 42 through a line 43 and a valve 45 to a cold trap 47. A vent line 49 with a valve 51 is connected to the cold trap. Also received through the extraction line 36 and through the valve 38 are amino acid fractions which are directed to the collector line 44, selector valve 45 and into a fraction collected 46 having a vent line 39 and valve 41.

In order to completely remove vapors from the reaction cup as well as the reaction chamber during the reaction cycle, both the extraction line 36 to the cup and the vent line 52 to the chamber must be vented at the same time. The chamber vent line 52 is connected through valve 54 and line 53 to the waste container 42.

Reference should be made to U.S. Pat. No. 3,725,010 for a detailed description of the overall peptide/protein system with respect to the transfer of the solvents and reagents to the reaction cell as well as for more detail with respect to the transfer of the vapors, solvent and reactants to either the fraction collector or to the waste receptacle.

The evacuation or removal of any waste, by-product vapors or reactants is accomplished by the positive pressure of the inert gas flowing into the reaction cell and out through the extraction line 36 and vent line 52. Furthermore, detail with respect to the valving operations of the system 32 and 34 to select and transfer the proper reagent or solvent at the proper time during sequencing cycle is shown in detail in the above referenced patent. The operation of this valving system is shown actuated by a vacuum system, but it could be operated by other means such as inert gas pressure or a solenoid arrangement. Therefore, the requirements for the vacuum pumps and vacuum lines in the arrangements shown in the referenced patent can be eliminated.

With respect to the operation of the peptide/protein system, a sample of polypeptide chain solution is placed in the reaction cell 12 which is a rotating glass cup. The solution assumes the form of a thin film on the inner wall 48 of the reaction cup as a result of the gravitational as well as centrifugal forces generated while the cup or cell 12 is being spun by the motor 14. The solvent within the film is removed as a vapor by the flow of positive pressure inert gas through the transfer line 18 which is preheated in the heater 24 as it enters the heated reaction chamber 10. The positive inert gas enters at the bottom 50 of the cup and flows over the thin film on the interior wall 48 and is exited through extraction line 36, valve 38 and waste line 40 to the waste receptacle 42, as well as through the chamber vent line 52 and valve 54 to the waste receptacle 42.

Phenyl isothiocyanate (PITC) or other suitable coupling agent is added in solvent such as heptane through the transfer line 28 and into the reaction cell 12 where it forms a thin film within the cup or cell 12. A major portion of the solvent such as heptane is removed by the flow of the inert gas into and over the thin film to the waste receptacle 42. The PITC remains as a thin film over the sample film.

A buffer of suitable pH and composition for the Edman chemistry is delivered through the transfer line 28 and into the reaction cell 12. The exit to the waste receptacle 42 is open via the valve 38 during this delivery of the suitable buffer to maintain a uniform pressure differential and to accomplish the repetitive delivery volume. The valve 38 is then closed and a coupling reaction is allowed to take place in the closed reaction chamber 10.

When the coupling reaction is completed, the volatile portion of the reactants is removed with the flow of the inert gas through the transfer line 18 and into the reaction cell for removal through the extraction line 36 and the chamber vent line 52. The semi-dried film within the reaction cell 12 is then washed with benzene, benzene and ethyl acetate or other suitable solvents through transfer line 28 to extract excess coupling agent and its by-products through the extraction line 36 by the positive pressure inert gas. The excess solvent is also removed with the inert gas flow. Further solvent extraction to remove buffer by-products is achieved by the delivery of ethyl acetate or other suitable solvent through the transfer line 28.

The thin film containing the phenylthiocarbamyl derivatized polypeptide chain is now dried with the flow of the inert gas through the line 18 and over the cup inner wall 48 and through a vent line 52 controlled by the valve 54. A cleavage acid is then delivered through the transfer line 28 over the thin film within the reaction cell to remove the amino terminal residue as an anilinothiazolinone derivatized amino acid (ATZ). The cleavage acid vapor is removed by the gas flow through the line 18. A solvent is then delivered through the transfer line 28 to extract the cleaved ATZ from the poypeptide chain. The solvent conveys the derivative to the fraction collector 46 through the extraction line 36, the valve 38, the collector line 44, and selector valve 45.

Figure 2:
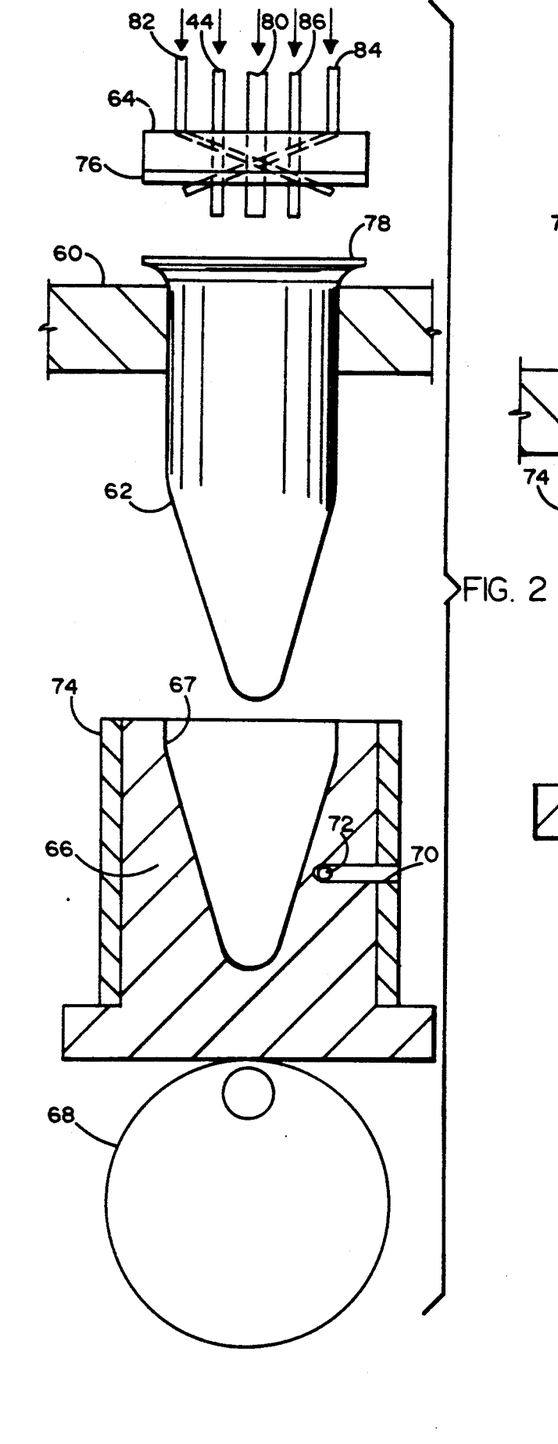
FIG. 2 is a side elevational view of the automatic conversion chemistry device prior to delivery head engagement with the tube.

Reference is made to FIG. 2 which shows in more detail the fraction collector 46. Included in this arrangement is a fraction collector rack 60 which contains a plurality of fraction collection tubes or second reaction cells 62. The rack 60 is operated by an automatic mechanism (not shown) wherein each tube 62 is advanced to a position under the delivery head 64 for each chemistry conversion process. The fraction collection tubes are preferably designed to be disposable.

Located below the tube 62 when it is positioned below delivery head 64 is a thermoelectric temperature control member 66 having a recess 67 designed to engage the lower portion of the fraction collector tube 62. The temperature control member 66 is designed to move vertically toward and away from the fraction collector tube which is situated in the rack 60. The movement of the temperature control member 66 is guided by support means (not shown). The driving mechanism for moving the temperature control member 66 is a cam apparatus 68 (shown schematically). It should be noted, however, that other types of arrangements could be utilized for providing the necessary vertical movement in the temperature control member. One approach could possible be through some type of solenoid arrangement or through some type of piston arrangement. Located within a well 70 in the temperature control member 66 is a thermistor 72 for sensing the temperature of the control member 66. The exterior of the temperature control member 66 has an insulating layer 74 which insulates the generated heat so that adjacent tubes are not affected during the reaction process.

The delivery head 64 has a resilient sealing surface or sealing element 76 which is designed to receive the upper end 78 of the collection tube 62. When the fraction collection tube 62 is in its proper orientation or placement with respect to the delivery head 64 and the temperature control member 66, sensing signals are sent to the microprocessor to activate the cam drive mechanism 68 to move the temperature control member 66 vertically upward so that the recess 67 in the member 66 will receive the lower portion of the collector tube 62.

Figure 3:
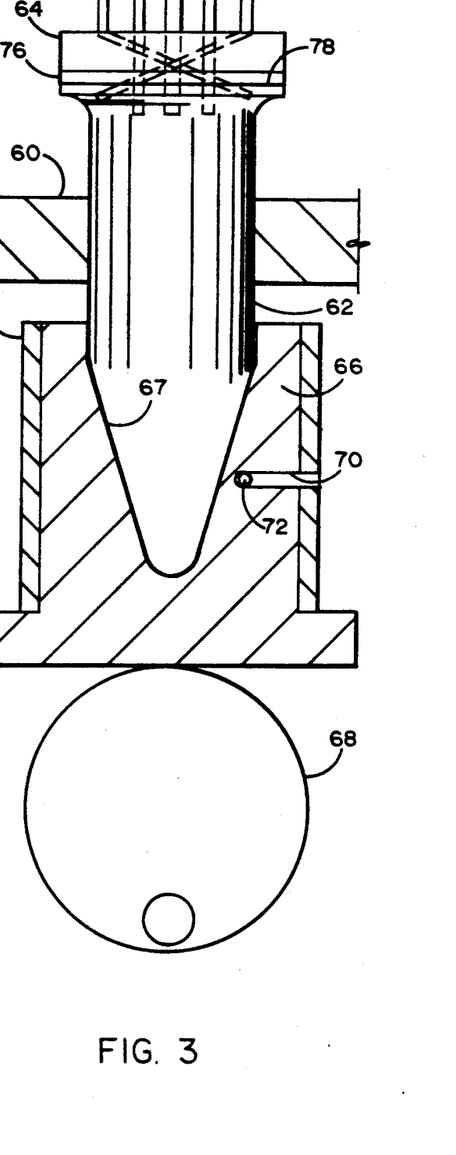
FIG. 3 is a side elevational view of the automatic conversion chemistry device as shown in FIG. 2 showing tube engagement with the delivery head.

Attention is directed to FIG. 3, showing the orientation of the temperature control member 66 with respect to the fraction collector tube 62. As the temperature control member 66 moves upward, it not only encases the tube 62, but also moves the tube slightly upward so that its upper end 78 engages the sealing element 76 of the delivery head 64. This will form a seal between the collector tube 62 and the delivery head 64.

Once the fraction collection tube or collector unit 62 is in its proper orientation with respect to both the delivery head 64 and the temperature control member 66, effluent from the spinning cup 12 containing the anilinothiazolinone derivative is transferred through the tubing 36, the valve 38 and the line 44 into the fraction collection tube. The central tubing 80 acts as a vent to the waste reservoir 42. However, if this exemplary sequencer system utilized a vacuum as in the system in U.S. Pat. No. 3,725,010, the vent port 80 would be the vacuum port. Inert gas enters through the ports 82 and 84 tangentally to the wall of the tube to create a vortex to not only speed up evaporation but also enhance the mixing of the sample in the tube as well as helping to wash the sample down the wall of the tube. Evaporative cooling of the tube contents is sensed by the thermistor 72 in well 70 of the temperature control member 66. The cooling effect of the evaporation is compensated by the heating from the thermoelectric device which constitutes the temperature control member 66.

After the removal of the solvent by the inert gas, an aqueous acid is delivered through the port 86 to initiate the conversion chemistry. The tube is then heated to provide the necessary heat to its internal contents to commence the conversion reaction. This heating is accomplished by the thermoelectric device of the temperature control member. After the conversion reaction is completed to yield the phenylthiohydantoin derivative, inert gas again enters through the ports 82 and 84 to evaporate the liquid and drive the vapor out of the tube to the waste reservoir through the vent line 80. The heating of the tube is discontinued.

Once the thermoelectric temperature control member 66 is lowered by the activation of the cam 68, the fraction collector rack 60 is advanced to the next fraction collection tube 62. The next chemistry conversion reaction is ready to begin once the temperature control member 66 is engaged with the tube and moves it into sealing engagement against the sealing element 76 of the delivery head 64.

Figure 4:
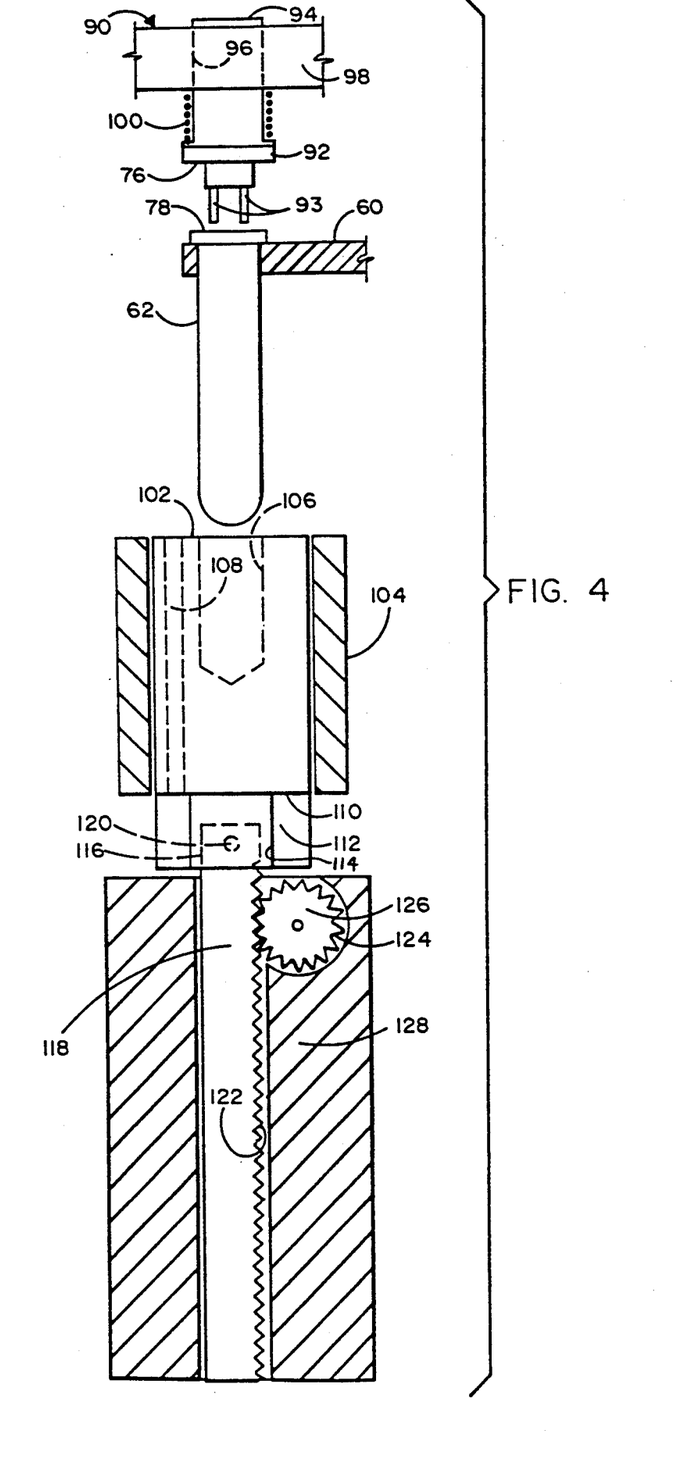
FIG. 4 is a side elevational view of an alternate embodiment of the present invention with the tube position prior to engagement with the delivery head.

An alternate embodiment of the present invention is shown in FIG. 4. This alternate embodiment is another embodiment of a fraction collector system which provides and allows for the conversion process to occur automatically and within the fraction collection tube. Therefore, this embodiment can be utilized with respect to FIG. 1 as the fraction collection unit 46. A fraction collector tube rack 60 contains a plurality of disposable fraction collection tubes 62. Included in the system is a delivery head assembly 90 which includes a delivery head 92 having delivery ports similar to the delivery head 64 in the embodiment of FIGS. 2 and 3. This delivery head system 92 has ports which represent respectively inert gas delivery, acid delivery, vent and derivative delivery. If the overall sequencer system is one which utilizes a vacuum, the vent port will also act as the vacuum port. The inert gas port may or may not be oriented for tangential impact on the tube wall as with ports 82 and 84 in FIG. 2. The delivery head 92 is mounted on a cylindrical sliding holder piston 94 which slides within an aperture 96 of the main delivery head support 98. The delivery head 92 is spring biased by a spring 100 away from the support 98. When a force is applied on the delivery head 92 toward the support 98, a spring 100 will compress somewhat as the cylindrical holder member slides upward within the aperture 96.

Located immediately below the fraction collection tube 62 is a temperature control member 102 which is slidably mounted within a sleeve 104. Located within the temperature control member 102 is a recess 106 designed for receipt of the lower portion of the fraction collection tube. Also located within the temperature control member 102 is a cartridge heater 108. However, it should be noted that the member 102 could also be a thermoelectric device as shown with respect to the embodiment shown in FIGS. 2 and 3. Attached to the bottom 110 of heater block 102 is an insulator connecting member or block 112 which has a slot 114 which is designed to receive a flat top flange 116 located at one end of a gear rack 118. The gear rack 118 is interconnected to the insulator block 112 by a pin 120 which allows some pivotal or relative movement between the gear rack 118 and the insulator block 112. It should be noted that the insulator block 112 is rigidly attached to the bottom 110 of the temperature control member 102.

The relative movement between the gear rack 118 and the insulator block 112 is desirable when the rack is moving the heater member 102 in a vertical direction toward and away from the fraction collection tube 62. The gear rack 118 is preferably a cylindrical rack having on one surface a plurality of gear teeth 122 which are designed to engage with the teeth 124 of the pinion gear 126. The gear rack 118 is mounted within a cylindrical sleeve 128 which provides guidance as it moves in a vertical direction as will be explained.

Figure 5:
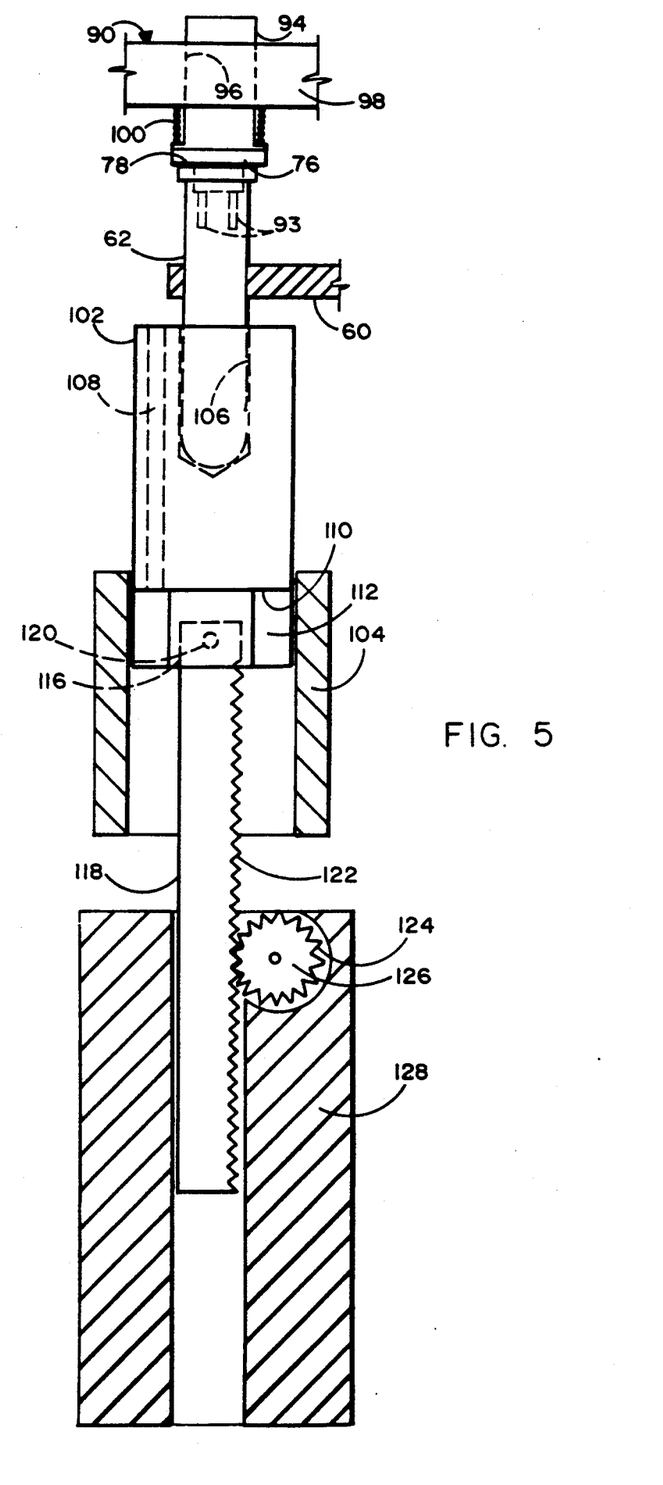
FIG. 5 is a side elevational view of the alternate embodiment shown in FIG. 4 showing the tube engaged with the delivery head.
Figure 6:
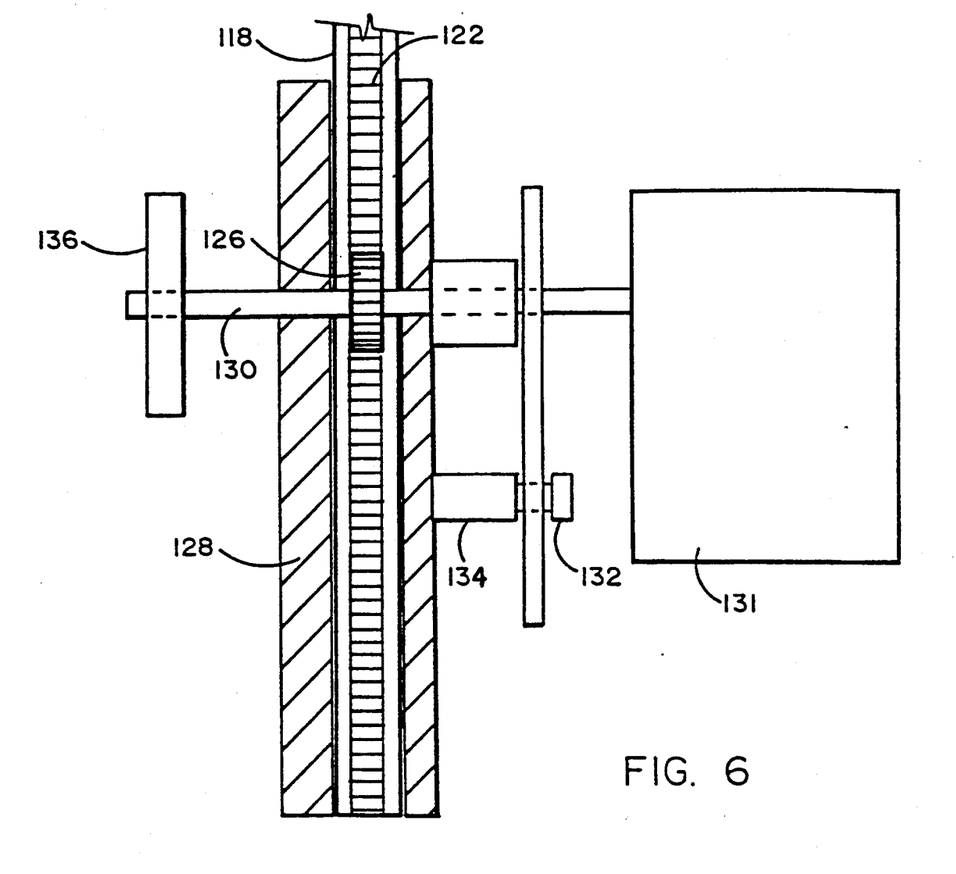
FIG. 6 is a side elevational view of the drive system for the alternate embodiment of FIGS. 4 and 5.

As shown more clearly in FIG. 6, the pinion gear 126 is connected by a shaft 130 to a motor 131. The gear rack sleeve 128 is mounted onto the motor by the bolts 132 and spacers 134. Rotation of the shaft will result in movement of the gear 126 which, in turn, causes the gear rack 118 to move vertically in an upward or downward direction. When the tube 62 is shown in a position with respect to FIG. 4, the microprocessor will instruct the motor to activate and cause the gear 126 to rotate in a direction to cause the gear rack 118 to move upward to the position shown in FIG. 5.

Figure 7:
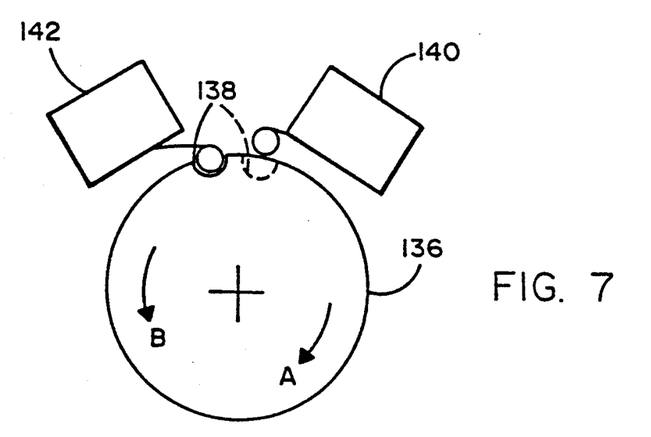
FIG. 7 schematically shows a cam control to limit the movement of the drive system for the alternate embodiment.

The amount of movement of the gear rack is controlled by a cam member 136 in FIG. 6. This cam operates on the same shaft 130 which is driven by the motor 131. As shown in FIG. 7, the cam 136 is shown schematically with a detent area 138 which is designed to engage one or the other of two limit switches 140 or 142. When the cam moves in the direction of the arrow "A", its limit in rotation will be stopped when the switch 142 contacts the detent 138. Similarly, when the cam 136 rotates in the direction of the arrow "B", the gear rack will move until the detent 138 engages the switch 140. The preferred design makes the operation throw of the gear rack by less than one turn of the cam 136. Therefore, the limit of the movement of the temperature control member 102 as shown in FIG. 5 is controlled by the movement of the detent 138 into engagement with the correct switch 140 or 142, depending upon the direction of the movement of the rack.

As the gear rack 118 moves the temperature control member 102 upward, it engages the lower portion of the tube 62 and moves it further upward so that the upper end 78 of the tube firmly engages the seal member 76 on the delivery head 92. After the conversion process has been completed, the motor 131 is activated in the reverse direction so that the gear rack will be tracked downward bringing the temperature control member downward so that the upper end 78 of the tube is disengaged from the delivery head 92. Further, as the temperature control member moves downward into its stationary sleeve 104, the fraction collection tube 62 can then be indexed away from the delivery head and allow the rack 60 to bring a new tube into position for the next conversion process. The downward movement of the rack is again limited by the control of the cam 136 and the engagement of the detent 138 with the respective switch 140 and 142.

The tube in which the conversion chemistry or reaction has occurred may then move beyond the sequencer apparatus for storage. The contents have been reduced to a dry state which further enhances its stability rather than if it were left in a solvent. The fraction may reside in each particular fraction collector tube for a variable length of time to await identification.

The overall operation of the present invention is accomplished by the use of a programmable controller which is designed to perform the desired temperature profile, time delivery of reagents and the time delivery of inert gas, the positioning of the tubes at the delivery head and the positioning of the temperature control block or a thermoelectric device. This control can be accomplished by the utilization of microprocessor capabilities that are utilized in the existing sequencer instrument prior to the incorporation of the present automated chemistry conversion device.

The fraction collection device of the present invention can be optionally maintained under conditions of inert gas atmosphere, vacuum and/or refrigeration. It is, however, important that oxygen be excluded in the operation of this chemistry and the use of this automatic chemistry conversion reaction device provides the capability of maintaining the exclusion of oxygen.

What is claimed is:

1. An apparatus for conducting chemical reactions using reagents and solvents to react with a sample, said apparatus comprising:
   a reaction vessel for containing a sample;
   means for transferring reagents and solvents to said reaction vessel;
   a fraction collector comprising a delivery head and a plurality of containers, each container being removable from said apparatus to provide a storage vessel for a product of a reaction;
   means for sequentially positioning each said container in a sealed relationship with said delivery head in said fraction collector and for removing each said container from sealed relationship with the delivery head when it is positioned in sealed relationship with the delivery head;
   means for transferring a reaction product from said reaction vessel to said delivery head and thence to each said container when it is positioned in sealed relationship with the delivery head; and
   means for conducting a reaction in each said container when it is positioned in sealed relationship with the delivery head.

2. The apparatus as defined in claim 1, wherein each said container is a fraction collector tube.

3. The apparatus as defined in claim 2, wherein said delivery head includes means for receiving each said fraction collector tube in sealed relationship therewith and a plurality of delivery ports.

4. The apparatus as defined in claim 3, further comprising means for controlling the environment within each said fraction collector tube when it is positioned in sealed relationship with the delivery head.

5. The apparatus as defined in claim 1, further comprising means for sequentially moving each said container to said positioning means and away from said positioning means.

6. The apparatus as defined in claim 5, wherein said moving means comprises means for holding a plurality of said containers, said holding means being able to move each said container to said positioning means for vertical movement into sealed relationship with the delivery head while simultaneously moving another said container away from said positioning means.

7. The apparatus as defined in claim 1, wherein said positioning means comprises means for vertically moving each said container into and out of sealed relationship with said delivery head.

8. The apparatus as defined in claim 7, wherein said means for vertically moving each said container comprises an engaging member for sequentially receiving a lower portion of each said container to hold each said container for vertical movement, said member including temperature control means for controlling temperature within each said container when it is in sealed relationship with the delivery head.

9. An automated polypeptide sequencing apparatus comprising:
   a reaction chamber for containing a sample;

a collector unit in fluid communication with said reaction chamber comprising a delivery head and a plurality of containers for receiving a thiazolinone amino acid product from said reaction chamber, each container being removable from said apparatus to provide a storage vessel for a product of a reaction;

means for fluid communication of gas, reagents, and solvents with said reaction vessel and said collector unit;

first transfer means for selectively transferring gas, reagents, and solvents to said reaction chamber for coupling and cleavage reactions to produce a thiazolinone amino acid product;

means for sequentially positioning each said container in a sealed relationship with said delivery head in said fraction collector to receive a thiazolinone amino acid product from the reaction chamber through the delivery head and for removing each said container from sealed relationship with the delivery head when it is positioned in sealed relationship with the delivery head, said delivery head comprising a sealing element for forming a seal with each said container when it is positioned in sealed relationship therewith, said delivery head also comprising at least one port configured to deliver a fluid to each said container in a tangential manner to create a vortex therein when it is positioned in sealed relationship with the delivery head;

second transfer means for selectively transferring a thiazolinone amino acid product from said reaction chamber, gases, reagents, and solvents to said delivery head and thence to each said container when it is positioned in sealed relationship with the delivery head to obtain conversion of a thiazolinone amino acid product to a phenylthiohydantoin product in each said container when it is positioned in sealed relationship with the delivery head, said second transfer means including means for introducing at least a first gas through said delivery head to each said container to at least partially evaporate and provide evaporative cooling of a phenylthiohydantoin product therein when it is positioned in sealed relationship with the delivery head;

thermistor means for sensing evaporative cooling in each said container when it is positioned in sealed relationship with the delivery head; and thermoelectric heating means for heating each said container when it is positioned in sealed relationship with the delivery head to compensate for evaporative cooling.

* * * * *